(12) United States Patent  
de Wekker

(10) Patent No.: US 8,568,419 B2
(45) Date of Patent: Oct. 29, 2013

(54) NAVIGATION SYSTEM FOR ORTHOPAEDIC SURGERY

(75) Inventor: Erwin de Wekker, Amsterdam (NL)

(73) Assignee: Hipsecure B.V., Amsterdam (NL)

( * ) Notice: Subject to any disclaimer, the term of this patent is extended or adjusted under 35 U.S.C. 154(b) by 119 days.

(21) Appl. No.: 13/311,610

(22) Filed: Dec. 6, 2011

(65) Prior Publication Data
US 2012/0190971 A1 Jul. 26, 2012

(30) Foreign Application Priority Data

Jan. 25, 2011 (EP) .................................... 11152026

(51) Int. Cl.
A61B 17/58 (2006.01)

(52) U.S. Cl.
USPC ............................................ 606/91; 606/130

(58) Field of Classification Search
USPC ............................................ 606/91, 102, 130
See application file for complete search history.

(56) References Cited

U.S. PATENT DOCUMENTS

| | | | |
|---|---|---|---|
| 3,262,452 | A | 7/1966 | Hardy et al. |
| 5,037,424 | A | 8/1991 | Aboczsky |
| 5,141,512 | A | 8/1992 | Farmer et al. |
| 6,063,124 | A | 5/2000 | Amstutz |
| 6,302,890 | B1 | 10/2001 | Leone, Jr. |
| 6,395,005 | B1 | 5/2002 | Lovell |
| 6,623,488 | B1 | 9/2003 | Leone, Jr. |
| 2004/0073225 | A1 | 4/2004 | Subba Rao |
| 2004/0210233 | A1 | 10/2004 | Yoon et al. |
| 2005/0107799 | A1 | 5/2005 | Graf et al. |
| 2005/0149050 | A1 | 7/2005 | Stifter et al. |
| 2005/0203540 | A1 | 9/2005 | Broyles |
| 2006/0161167 | A1 | 7/2006 | Myers et al. |
| 2006/0217737 | A1 | 9/2006 | Iversen |
| 2008/0077004 | A1 | 3/2008 | Henning |
| 2008/0132903 | A1 | 6/2008 | Yoon |
| 2009/0105714 | A1 | 4/2009 | Kozak |
| 2009/0171370 | A1 | 7/2009 | Yoon et al. |
| 2009/0306679 | A1 | 12/2009 | Murphy |
| 2011/0060339 | A1 | 3/2011 | De Wekker |

FOREIGN PATENT DOCUMENTS

EP 1402839 3/2004
(Continued)

OTHER PUBLICATIONS

Extended European Search Report, mailed Jun. 28, 2011 in connection with European Patent Application No. 11152026.8.
Machine translation of description and claims of FR910078.
(Continued)

Primary Examiner — Nicholas Woodall
(74) Attorney, Agent, or Firm — Westman, Champlin & Koehler, P.A.

(57) ABSTRACT

A navigation system for placing an implant in orthopedic surgery is provided, comprising an orientation apparatus and a reference apparatus. The reference apparatus comprises an anchor for fixing the reference apparatus to a predetermined feature of the subjects body and an indicator for indicating at least one reference plane or axis. The orientation apparatus comprises a number of probes for contacting a number of predetermined features of a subjects body and defining a plane. The orientation apparatus and/or the reference apparatus comprises at least one connector for connecting the orientation apparatus and the anchor such that, when connected, relative translation of the connector and the anchor along a predetermined direction with respect to the plane defined by the probes is allowed and relative rotation of the connector and the anchor about that predetermined direction is prevented.

18 Claims, 6 Drawing Sheets

(56) References Cited

FOREIGN PATENT DOCUMENTS

| | | |
|---|---|---|
| EP | 1920713 | 5/2008 |
| EP | 2067443 | 6/2009 |
| FR | 910078 | 5/1946 |
| JP | 2000000257 | 1/2000 |
| WO | 0121084 | 3/2001 |
| WO | 2006109983 | 10/2006 |
| WO | 2008118524 | 10/2008 |
| WO | 03077807 | 12/2011 |

OTHER PUBLICATIONS

Article L. Fabeck et al., A Method to Measure Acetabular Cup Anteversion After Total Hip Replacement, Acta Orthopaedica Belgica, vol. 65—Apr. 1999.

Abstract of JP 2000000257.

Article Riten Pradhan, Planar Anteversion of the Acetabular Cup as Determined From Plain Anteroposterior Radiographs, vol. 81-B, No. 3, May 1999.

Machine translation of description, claims and abstract of EP1402839.

Extended European Search Report, mailed Nov. 8, 2010 in connection with European Patent Application No. 10175817.5.

NAVIGATION SYSTEM FOR ORTHOPAEDIC SURGERY

PRIORITY CLAIM TO RELATED APPLICATIONS

This application is an original application under 35 U.S.C. §111(a) claiming priority to European Application No. 11152026.8, entitled "Navigation system for orthopaedic surgery", filed on 25 Jan. 2011, which application is incorporated herein by reference and made a part hereof in its entirety, and the benefit of priority of which is claimed herein.

TECHNICAL FIELD

The present invention relates to a navigation system for implanting an implant, e.g. an acetabular cup, in particular a system for accurately implanting a reference instrument, e.g. in a pelvis, which may serve as a guide for placing an implant during an orthopaedic surgical operation, e.g. for placing an acetabular cup during total hip surgery.

SUMMARY OF THE DISCLOSURE

This disclosure provides a reference system for orthopaedic surgery, in particular joint surgery, more in particular a system for placing an acetabular cup, with a focus on being user-friendly, accurate, simple, fast and cost-effective and without using computers and scans or other unnecessary manipulating mechanisms.

This disclosure provides a reference system for orthopaedic surgery, in particular for placing an acetabular cup, which is generally independent of movements of (joint parts of) the subject, e.g. the pelvis, during surgery.

The present disclosure forms or is part of a navigation system for placing an implant in orthopaedic surgery, and may for instance be used for placing an acetabular cup in total hip surgery.

The system comprises two parts; an orientation apparatus and a reference apparatus. The reference apparatus comprises an anchor for fixing the reference apparatus to a predetermined feature of the subjects body, and at least one indicator for indicating at least one reference plane and/or axis. The subject may be a human or an animal. The orientation apparatus comprises a number of probes, preferably three or more probes, for contacting a number of predetermined features of a subjects body and defining a plane. At least one of the orientation apparatus and the reference apparatus comprises at least one connector for connecting the orientation apparatus and the anchor such that, when connected, relative translation of the connector and the anchor along a predetermined direction with respect to the plane defined by the probes is allowed and relative rotation of the connector and the anchor about that predetermined direction is prevented. This allows fixing the anchor to the subjects body without a rotation with respect to the orientation apparatus.

The orientation apparatus aims to use a number of typical, specific features of the subjects body, in particular a human body, for a desired positioning of the reference apparatus. For this, physical contact with these specific features is used. E.g. for a pelvis, the anterior pelvic plane may be used for fixing the reference apparatus. The reference apparatus aims to clarify and/or make visible one or more axes and/or planes with a known relation to the plane defined by the specific features of the subjects body, so as to use them for accurately placing an implant, e.g. an acetabular cup in total hip replacement surgery.

In a particular embodiment, the orientation apparatus aims to use, by means of physical contact with three specific features of a pelvis, the anterior pelvic plane for fixing the reference apparatus and the reference apparatus aims to make visible for the surgeon during surgery, and in particular during placing an acetabular cup, one or more anatomic planes and/or or axes or planes with a predetermined relation to the anterior pelvic plane.

In a refinement, The at least one connector comprises a through hole defining the predetermined direction, and the anchor comprises at least a connection portion mated to the through hole. The direction of extension may define the predetermined direction. This facilitates intuitive understanding and use of the system. A through hole also provides strength.

In a further refinement, the through hole has a non-circular cross-sectional shape and the connection portion of the anchor has a mated non-circular cross-sectional shape. This facilitates preventing rotation of the anchor relative to the connector.

Advantageously, a probe comprises the at least one connector. This facilitates positioning the reference system with respect to a specific feature of the subjects body.

The predetermined direction may be substantially normal to the plane. This facilitates intuitive understanding and use of the system.

In an embodiment, the orientation apparatus comprises a first, second and third probe connected to each other with at least two connecting members, wherein the connecting members are adjustable such that the first probe may contact a first predetermined feature of the subjects body, e.g. the os pubis, the second probe may contact a second predetermined feature of the subjects body, e.g. the left spina iliaca anterior superior and the third probe may contact a third predetermined feature of the subjects body, e.g. the right spina iliaca anterior superior, concurrently. Thus, three features are concurrently contacted therewith spanning a unique plane. In the particular exemplified case, this is the anterior pelvic plane, but other planes may be defined also. More than three probes may improve definition of a plane or provide concurrent definition of plural planes.

In refinements, at least one connecting member may be length-adjustable and/or at least two connecting members may be arranged at an angle to each other, wherein the angle is adjustable and/or at least a portion of at least one of the connecting members extends offset from the plane and/or at least one probe of the orientation apparatus may be height-adjustable with respect to a least one other probe and/or at least one connecting member. This facilitates use of the system with different subjects and allows adapting if desired.

The reference apparatus may comprise plural anchoring portions for fixing it to the subjects body, in a particular embodiment the anchor may comprise two anchoring pins. This assists preventing rotation of at least the anchor of the reference apparatus with respect to the subjects body when fixed thereto.

Advantageously, the anchor and the indicator of the reference apparatus are irrotationally coupled together, preventing rotation of the indicator with respect to the anchor, and they may be releasably coupled together, which may facilitate fixing the reference apparatus to the subjects body.

The indicator of the reference apparatus may be arranged for indicating at least one plane.

The orientation apparatus and/or reference apparatus may be manufactured and sold together in a kit of parts, which may comprise further parts, and/or manufactured and sold as separate objects, e.g. for replacement.

One or more portions of the navigation system may be reusable or rather provided for single use.

A proper use of the system, e.g. for total hip surgery, comprises the following steps:

a) adjustment of the orientation apparatus with respect to the subjects body portion to be mapped such that the probes contact the specific features of the subjects body portion to be mapped, e.g. the features of the subjects pelvis defining the anterior pelvic plane b) rotation-stable fixing of the reference apparatus to the subjects body portion to be mapped, e.g. irrotational fixing of the reference apparatus the pelvis by connecting the reference apparatus with a connector of the orientation apparatus (e.g. insertion of the reference apparatus through a through hole in the orientation apparatus), such that the orientation apparatus remains in contact with the specific features of the subjects body (e.g. three features of the pelvis) during fixing of the reference apparatus c) removal of the orientation apparatus and leaving at least a portion of the reference apparatus d) optional manipulation of the subjects body portion into a desired position e) arranging the indicator on the anchor of the reference apparatus (depending on the specific embodiment of the disclosed reference apparatus)

f) positioning the implant, e.g. an acetabular cup or a trial, e.g. by means of a cup introducer as known in the art, preferably by one or more reference planes and/or reference axes indicated by the reference apparatus and/or positioning using a measurement tool e.g. as described in NL 1 037 265 by reference to one or more reference planes and/or reference axes indicated by the reference apparatus.

BRIEF DESCRIPTION OF THE DRAWINGS

The above-described aspects will hereafter be more explained with further details and benefits with reference to the drawings showing embodiments of the invention by way of example.

DETAILED DESCRIPTION OF EMBODIMENTS

Figure 1:
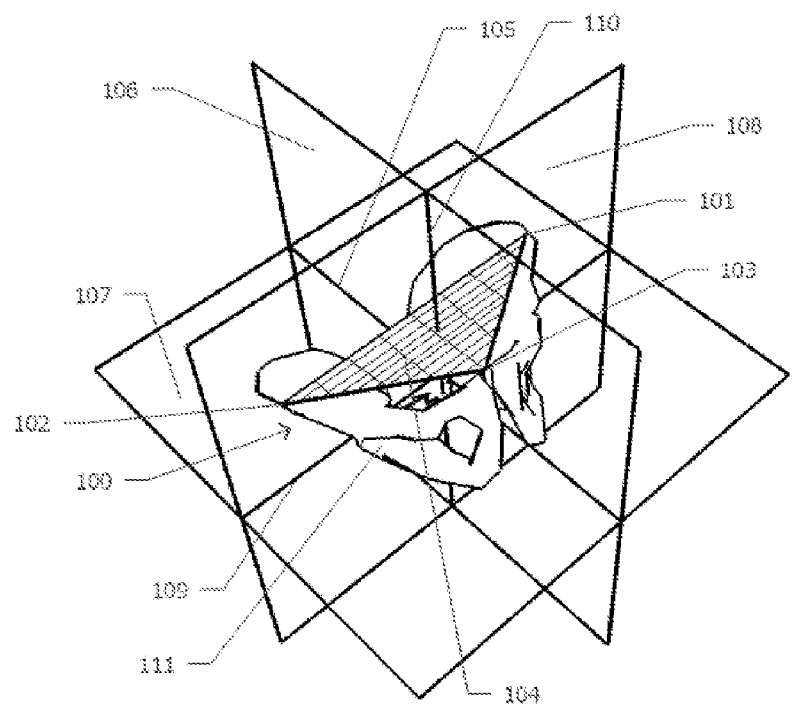
FIG. 1 shows a human pelvis with an anterior pelvic plane and two anatomical planes.

In the following description these and other aspects of the disclosure are discussed in detail with reference to the drawings.

It is noted that the drawings are schematic, not necessarily to scale and that details that are not required for understanding the present invention may have been omitted. The terms "upward", "downward", "below", "above", and the like relate to the embodiments as oriented in the drawings, unless otherwise specified. Further, elements that are at least substantially identical or that perform an at least substantially identical function are denoted by the same numeral.

In orthopaedic surgery, regularly implants are implanted, e.g. for replacement of worn and or painful joints. Such implants should be placed as accurately as possible. This, namely, increases the chances of patient satisfaction and accurate placement generally contributes to extension of useful service life of the implant. A specific example of the importance of accurate placement of an implant is provided by total hip surgery, in which a natural hip joint is replaced by and artificial joint.

The hip joint is formed by a ball-shaped femur head and a cup-shaped portion in the pelvic. When the natural hip joint is severely damaged, e.g. by old age or an affliction, an artificial hip joint may be placed, to reduce pain and/or to increase freedom of movement of the hip joint. Such procedure is called total hip surgery or -replacement. An artificial hip joint for total replacement comprises a portion replacing the femur head and a portion (the acetabular cup) that replaces the cup-shaped recess (acetabulum) in the pelvis.

A correct positioning of the acetabular cup is important, if not essential, for proper functioning of the artificial hip joint. In addition to restriction in the freedom of movement of the joint, an incorrect placement of the acetabular cup may cause a restricted service life time of the artificial joint, and it may even lead to luxation. In order to allow realising a correct placement the position in the pelvis the position of the pelvis during surgery should be known, and with it the position of the anatomic planes. One of the most reliable methods to provide a proper estimate of the position of the pelvis is orientation by use of the anterior pelvic plane. This plane, which is parallel to the frontal plane of the pelvis, is defined by three marked features of the pelvis, namely the os pubis, the left spina iliaca anterior superior and the right spina iliaca anterior superior.

The present disclosure assists, intra alia, to the procedure for accurate placement of an acetabular cup by means of rendering visible important planes, e.g. anatomical planes, and/or axes of a joint, in particular a pelvis. The disclosed navigation system is also suitable for other orthopaedic procedures, e.g. (total) shoulder surgery, (total) knee surgery, trauma surgery, spine surgery, or ankle surgery. Nevertheless, for purposes of explaining the relevance and operation of the system, the present disclosure primarily deals with total hip surgery, in particular to placing an acetabular cup.

A navigation system for placing an acetabular cup is described in US 2009 171370. The system uses a pelvis position seeker which clarifies the anterior pelvic plane through three marked points. At the moment the three points of the pelvis are in contact with three probes of the instrument, a plate coupled to the instrument indicates a plane that is parallel to the anterior pelvic plane. Next, a second instrument, a pelvis position indicator, is to be placed in the pelvis. This pelvis position indicator comprises a second plate which is to be arranged, by means of a manipulation mechanism (e.g. a ball joint), parallel and/or perpendicular to the plate of the pelvis position seeker. Thus, the pelvis position indicator clarifies the anterior pelvic plane or planes parallel thereto. Subsequently the pelvis position seeker must be removed and the surgery can be continued.

This system is involved and its use is time-consuming because a series of steps is needed for clarification of axes or planes perpendicular and/or parallel to the anterior pelvic plane. In addition, aligning the plate of the pelvis position indicator to the plate of the pelvis position seeker causes additional risks for inaccuracies. Further, due to the use of a ball joint and plates the navigation system becomes more costly and more sensitive for defects than should be necessary.

An optical navigation system for placing an acetabular cup is described in U.S. Pat. No. 5,141,512. The system also uses the anterior pelvic plane, in combination with a light source. This system is awkward and risky since the pelvis position instrument must be in contact with the three above-named points of the pelvis during the entire time needed for positioning an acetabular cup. This causes additional risks of infections and it hinders the working space of the orthopaedic surgeon. Also, the system is nearly impossible to use for orthopaedic surgeons preferring to perform surgery on a patient lying on its side (lateral decubitus position). Namely, in such position the instrument will be in the space of the pelvis which is used for fixing it by means of supports.

FIG. 1 shows a human pelvis 100 in supine position including an acetabulum 111 and three anatomic planes; the sagittal plane 106, the frontal plane 107 and the transverse plane 108. The intersections of these planes are formed by anatomic axes: the longitudinal axis 105, the transversal axis 109 and the sagittal axis 110. Further, three noted features of the pelvis which are palpable through the skin are indicated: a left spina iliaca anterior superior 101, a right spina iliaca anterior superior 102 and the os pubis 103. The triangle which results from a (imaginary) connection of these points defines the anterior pelvic plane 104. The anterior pelvic plane 104 is parallel to the frontal plane 107 of the pelvis 100. Since the frontal plane 107 is in a perpendicular relation to both the sagittal plane 106 and the transverse plane 108, the anterior pelvic plane 104 has the same perpendicular relation to the sagittal plane 106 and the transverse plane 108.

Figure 2:
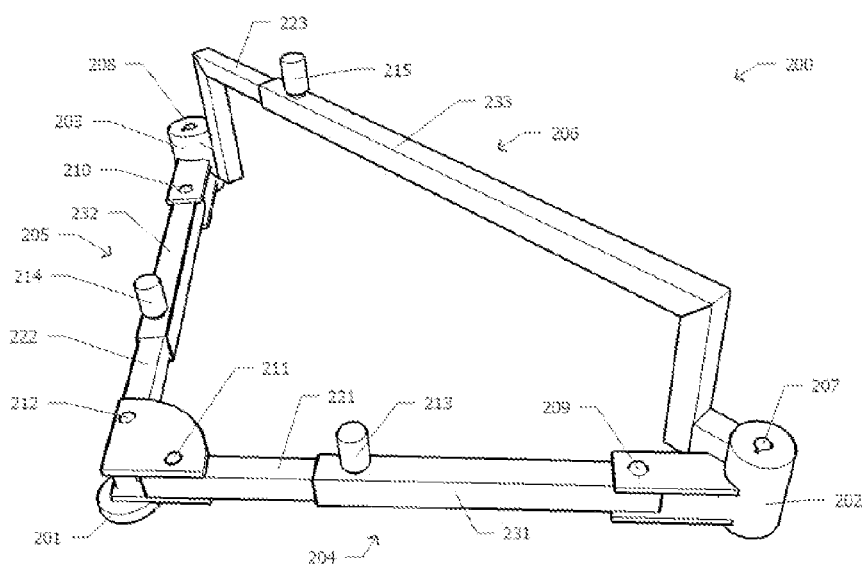
FIG. 2 shows an embodiment of an apparatus with which the anterior pelvic plane of a human pelvis may be localised.

FIG. 2 shows an embodiment of an orientation apparatus 200 according to the present disclosure, intended for localising the anterior pelvic plane 104 of different pelvises 100. In this embodiment the orientation apparatus 200 comprises three probes or contact bodies which are connected to each other: a probe 201 for contact with the os pubis 103, a probe 202 for contact with a left spina iliaca anterior superior 101 and a probe 203 for contact with a right spina iliaca anterior superior 102, but the probes may be configured for contacting other features of a subjects body. It is noted here that "contact" may mean palpating contact, i.e. with skin and possibly some subcutaneous tissue between a bony feature and the probe, but direct contact, e.g. transdermal penetrating contact or direct contact when the skin is opened surgically, may also be possible.

The probes are connected to each other with connecting members; a first adjustable member 204 between probes 201 and 202, a second adjustable member 205 between probes 201 and 203 and a third adjustable member 206 between probes 202 and 203. The shown adjustable members 204, 205, 206, comprise relatively narrower portions 221, 222 and 223 and relatively wider portions 231, 232, 233 which may slide over one another so that the separation between the probes 201, 202, 203 may be increased or reduced as desired. By screws 213, 214, 215 or other fasteners the adjustable members 204, 205, 206 may be at least partially released for adjustment or rather be fixed. Other adjustment means are also conceivable. Adjustable member 204 may rotate, here substantially independently, about a hinge 211 and a hinge 209. Adjustable member 205 may rotate about hinges 210 and 212. In another embodiment the hinging axis of hinge 211 may coincide with that of hinge 212.

By interaction of at least some of the above-mentioned parts the triangle that is formed between the probes 201, 202, 203 change shape and size. Thus, it is possible to localise the anterior pelvic plane 104 of different pelvises 100, which may differ in size and/or shape. A portion of the adjustable member 206 is offset from a plane comprising the other adjustable members 204, 205 and offset from the plane defined by the probes. An object of the height-offset portion in the adjustable member 206 is to prevent the belly of corpulent patients from becoming an obstacle. In another embodiment of the orientation apparatus 200 hinges not required, in principle, to vary the size and/or shape (different angles) of the triangle between the probes 201, 202, 203. This is for instance possible when the orientation apparatus is generally T-shaped (not shown). In such case only one or two adjustable members may be required to contact the three palpable features of the pelvis.

Figure 7:
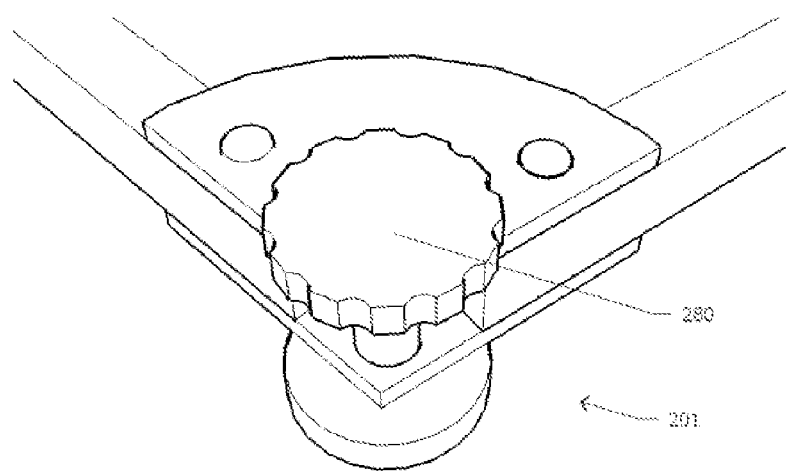
FIG. 7 is a close-up of a height-adjustable probe of an orientation apparatus.

In some cases the os pubis may be relatively hard to palpate. In particular in the case of relatively corpulent patients, the os pubis 103 may be located beneath a relatively thick layer of fat. In such case it may happen that when using the orientation apparatus 200 the abstract triangle spanned by the three probes 201, 202, 203 is not parallel to the anterior pelvic plane 104. In FIG. 7 a close-up of a possible embodiment of the probe 201 of the orientation apparatus 200 is shown. With such embodiment it is possible to circumvent the above-described problem. Here, probe 201 is height-adjustable by a screwing connection 280 as known in the art. Thus, the thickness of the fat layer on the os pubis may be taken into accounted (e.g. by estimating or measuring such thickness). By screwing the screw 280 inward or outward the right height of the probe 201 may be determined. Thus, the imaginary plane between the probes 201, 202, 203 may be brought parallel to the anterior pelvic plane. Such height-adjustable connection may be realised in different ways, known in the art. Possibly a degree-marking may be provided, or some other provision for indicating the angle between the direction defined by the connectors (here through holes 207, 208) and the imaginary plane defined by the probes 201, 202, 203. In another embodiment of an orientation apparatus 200 more than one, possibly all probes 201, 202, 203 are height-adjustable. This provides the option map the results of a measurement before a surgical operation to a measurement during surgery, e.g. a pelvis measurement on a standing patient vs. a substantially identical measurement on the patient lying down. This may be done by visualising and accounting for the angular difference between the plane to be identified (e.g. the anterior pelvic plane) and the direction of gravity by a standing patient, e.g. by means of a height-adjustable orientation apparatus (200). This enables, e.g. to ensure that a placed implant, e.g. an acetabular cup, has a particular position in a standing patient with respect to the direction of gravity (being parallel to a frontal plane of the body).

In probe 202 and probe 203 a left and right through hole 207, and 208, are visible, respectively, forming connectors for connecting an anchor of a reference apparatus 300. Through holes 207, 208 aim to guide an object. It is therefore advantageous when through holes 207 and/or 208 extend at least partially through the probes 201 and/or 203 since these are located over the spinae 101, 102 upon positioning of the orientation apparatus 200, but this is not essential. Both spinae 101, 102 are very well suited, in particular due to their shallow position under the skin, for insertion therein of (an anchor of) a reference apparatus. In the shown embodiment the longitudinal direction of both through holes 207, 208 perpendicular to (normal to) the imaginary plane defined by the probes 201, 202, 203, in particular the undersides or lowermost portions thereof when in use on a lying patient. This means that when the probes 201, 202, 203 are concurrently in contact with the three points 101, 102, 103 of the pelvis, the through holes 207 and 208 extend perpendicular to the anterior pelvic plane 104. Thus, the through holes 207, 208 extend parallel to a sagittal axis 110 and have a perpendicular relation to the transverse axis 109 and the longitudinal axis 105. In addition to a perpendicular relation to the plane defined by the probes 201, 202, 203 the through holes 207, 208 further have such a shape that an object having a mated shape, in particular at least a portion of an anchor, can only be introduced in such through hole 207, 208 rectilinearly, i.e. relative translation of the connector and the anchor along the predetermined direction with respect to the plane defined by the direction of extension of the through hole is allowed but relative rotation of the connector and the anchor about that predetermined direction is prevented.

Figure 3A:
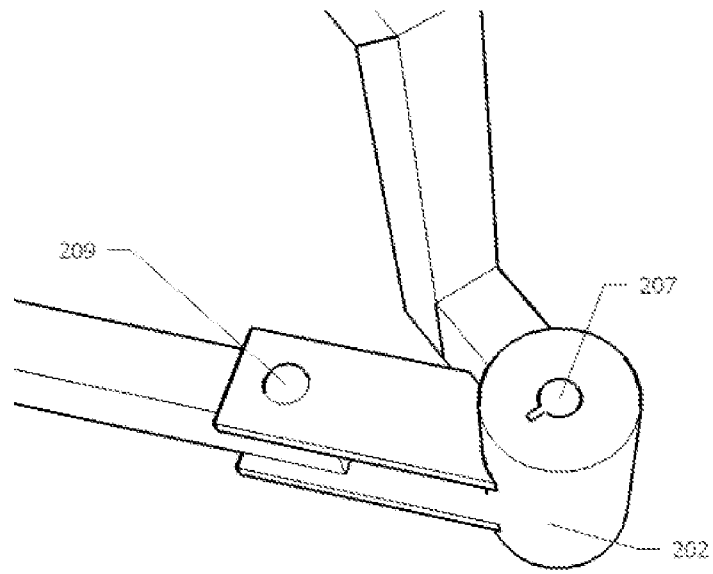
FIGS. 3A and 3B show different embodiments of rotation-stable introduction holes.
Figure 3B:
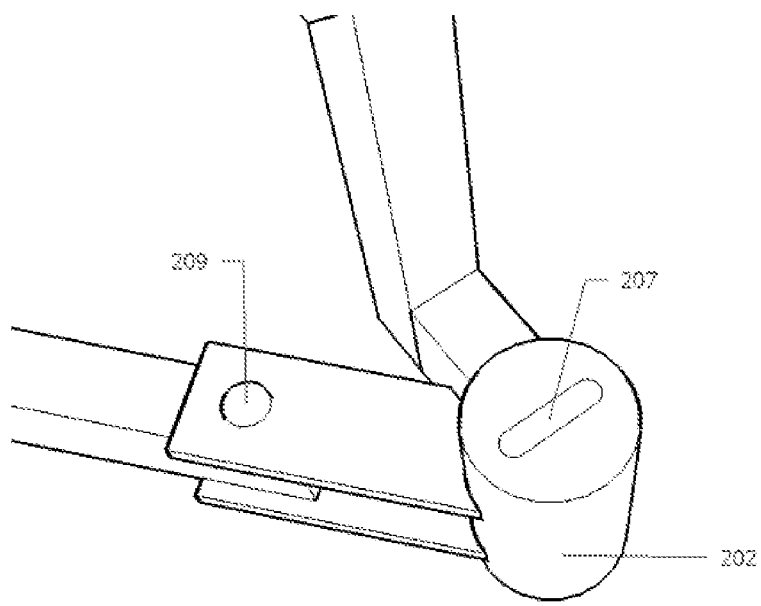

FIGS. 3A and 3B show close ups of two embodiments of a probe 202 having a connector in the form of a through hole 207 having a non-circular cross sectional shape when seen along the direction of extension of the through hole.

FIGS. 4A-4D show different embodiments of a reference apparatus 300. An object of such reference apparatus 300 is to clarify (a portion of) the anatomic planes 106, 107, 108. Other embodiments may make another plane visible. Such clarification may be provided by fixing the reference apparatus 300 to the subjects body, here to the pelvis 100, e.g. in particular to a spina iliaca anterior superior 101, 102, preferable at the side where the surgery is performed, e.g. at the side where surgery is performed on an acetabulum 111. By using the orientation apparatus 200 such fixing may be very accurate; due to the rectilinear motion enforced by the connector, here the through hole 207, the anchor 301 will be arranged in the predetermined direction with respect to the imaginary plane, here substantially normal to the anterior pelvic plane 104.

Figure 4A:
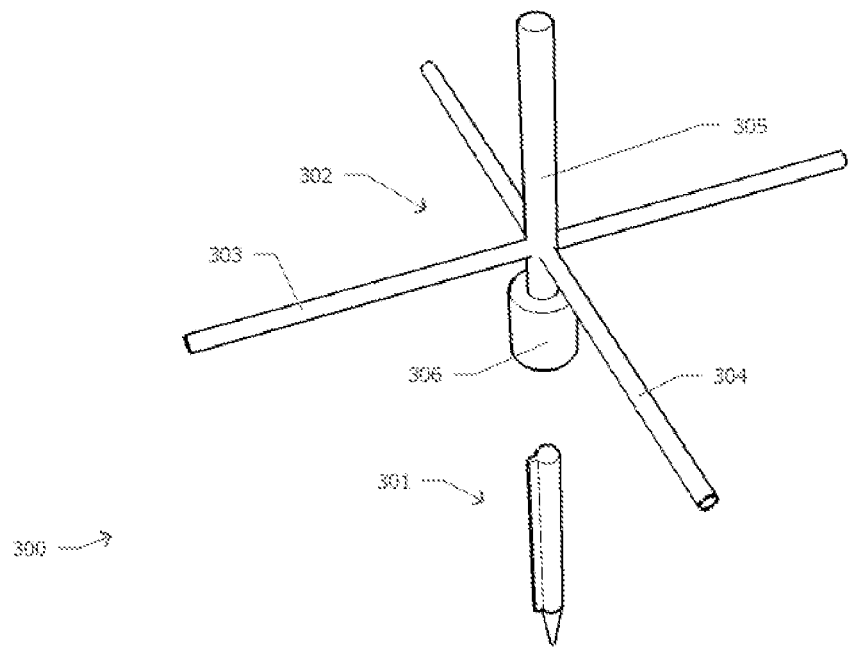
FIGS. 4A-4D show different embodiments of a reference apparatus.
Figure 4B:
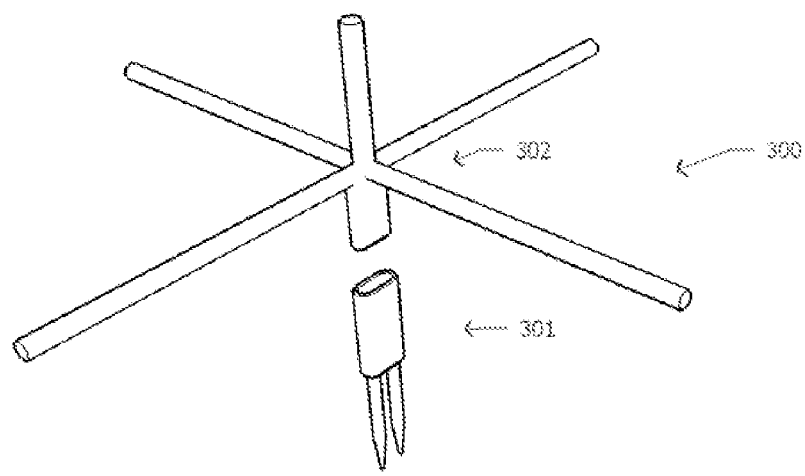
Figure 4C:
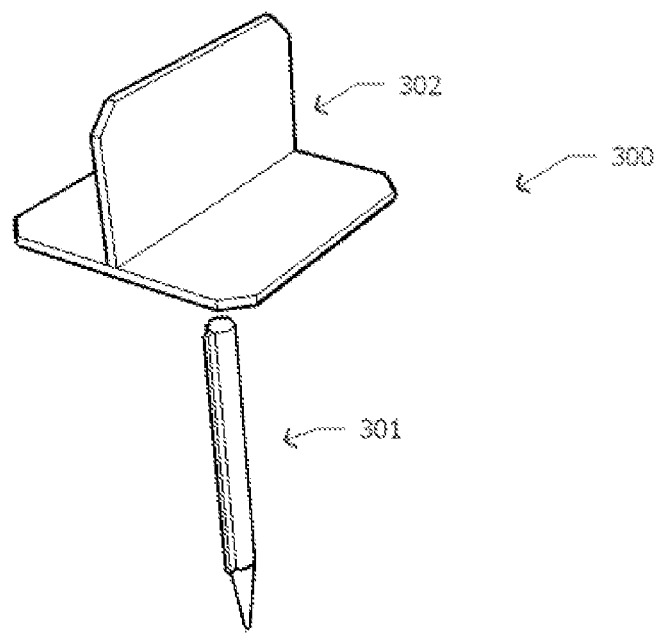
Figure 4D:
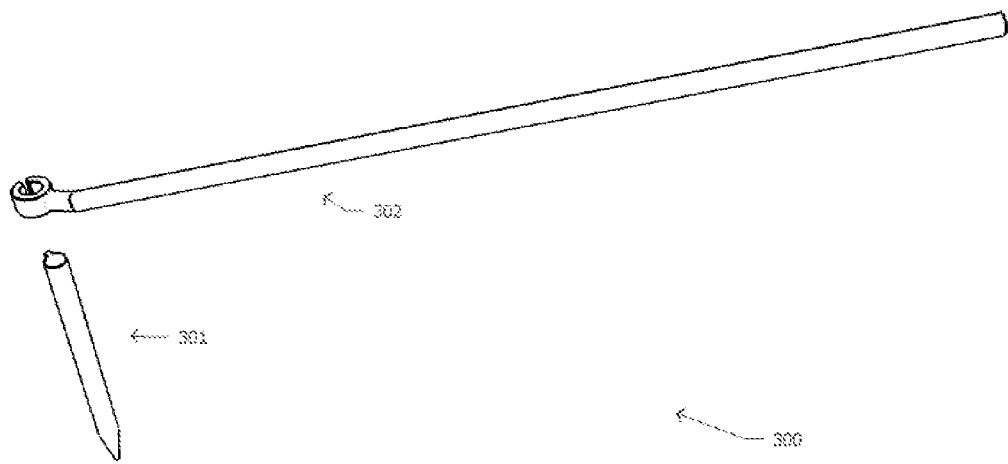

FIG. 4A shows a reference apparatus comprising an anchor 301 and an indicator 302 which are releasably connectable to each other. In this case, the indicator 302 comprises a plurality of mutually perpendicular rods for indicating axes which upon proper fixation of the reference apparatus 300 may extend parallel to the anatomic axes 105, 111, 109. The anchor 301 has a substantially pin-shaped portion. The anchor 301 is formed such that it has a mated or complementary shape to the shape of the through hole, such that the anchor 301 can be coupled to a connector preventing mutual rotation. Here in particular, the anchor can be inserted into and translated through a though hole 207 without rotation. FIGS. 4C and 4D show different embodiments of a reference apparatus 300, but all having an anchor 301 of the same basic shape, mated to the cross sectional through hole 207 of FIG. 3A, the through hole 207 having a shape which is the negative of the (positive) cross sectional shape of the relevant connecting portion of the anchors 301. FIG. 4B shows a reference apparatus 300 wherein the anchor 301 comprises plural juxtaposed pins, here two pins, which advantageously are parallel to each other. Such "double pin" anchor 301 may be introduced irrotationaly through a through hole 207 as shown in FIG. 3B. Instead of a second pin a screw may be provided. Also, plural adjacent screws may be used for fixing the anchor. Different mated shapes of connectors and anchors can be used, e.g. elliptical, triangular, rectangular, hexagonal etc., or having one or more a substantially shafts which may have a number of protrusions (such shaft with one protruding rib is shown in FIGS. 4A, 4C and 4D) etc.

Figure 8:
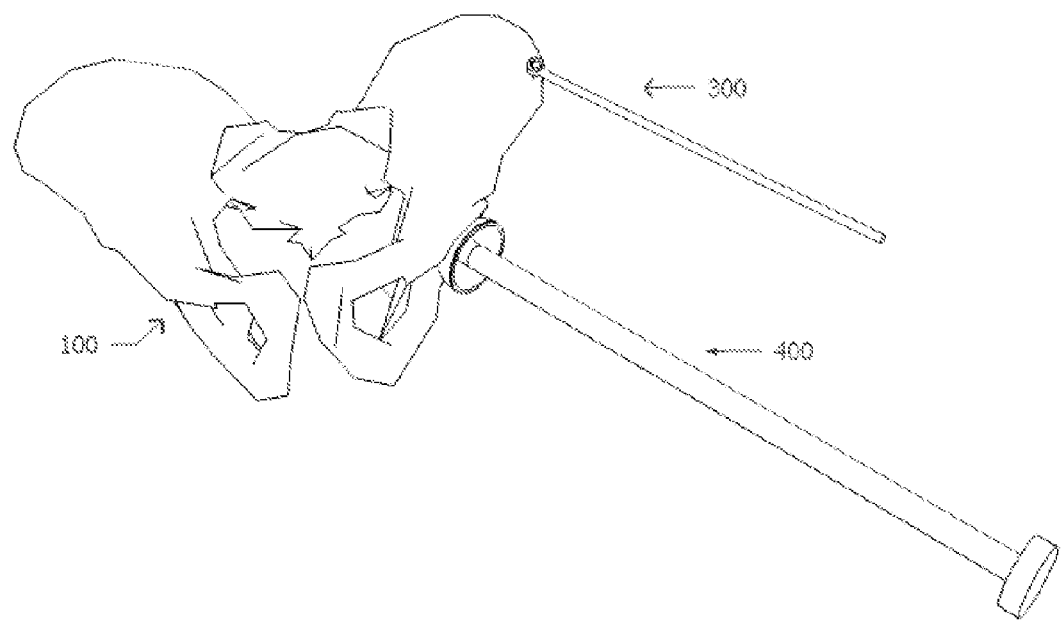
FIG. 8 shows introduction of an acetabular cup into a pelvis which is provided with the reference apparatus of FIG. 4D, wherein the direction of introduction is substantially parallel to an axis indicated by the reference apparatus.

In the reference apparatus 300 of FIG. 4C the indicator 302 comprises two mutually perpendicular planes. In the reference object 300 of FIG. 4C the indicator 302 comprises a single shaft indicating a particular axis with a preferred direction for implanting an acetabulum cup in a pelvis, see also FIG. 8 and below. FIG. 4D also shows that the indicator 302 comprises a generally C-shaped connector for a releasable connection to the anchor 301. Such connector may also be provided in an orientation apparatus 200. In similar fashion any other desired predetermined angle between the orientation apparatus and the anchor (and/or the indicator) may be established and provided.

Figure 5:
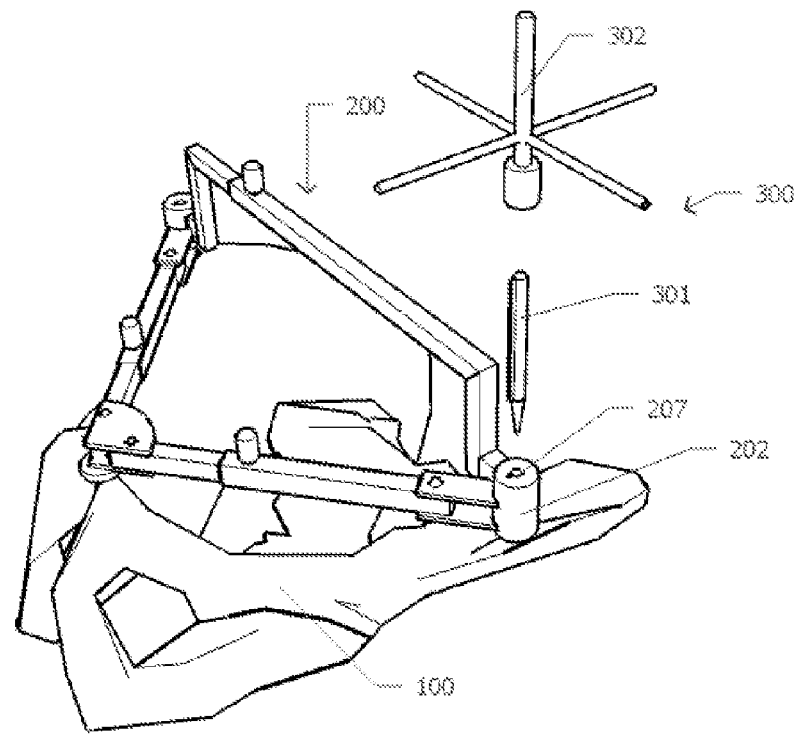
FIG. 5 shows a human pelvis with an orientation apparatus on it, wherein a reference apparatus is indicated (exploded view) on a left probe.

FIG. 5 shows a pelvis 100 with an orientation apparatus 200 according to FIG. 2 of which the probes 201, 202, 203 are in contact with three features of a pelvis, here the three points discussed before (spinae 101 and 102 and os pubis 103). Above probe 202 with connector 207 an exploded view is shown of a reference apparatus 300, comprising an anchor 301 and an indicator 302. By connecting the anchor to the orientation apparatus 200, here by inserting the anchor 301 through the connector realised as a through hole 207, the anchor 301 may be oriented substantially perpendicular to the anterior pelvic plane (not shown) and be fixed to the pelvis, here by insertion into (the left spina iliaca anterior superior 101 of) the pelvis 100. Since relative rotation between the orientation apparatus and the anchor, rotation of the anchor relative to the subjects body portion, here the pelvis, is prevented. After optional removal of the orientation apparatus 200 and (irrotational) connecting of the indicator 302 to the anchor 301 the situation shown in FIG. 6 results.

Figure 6:
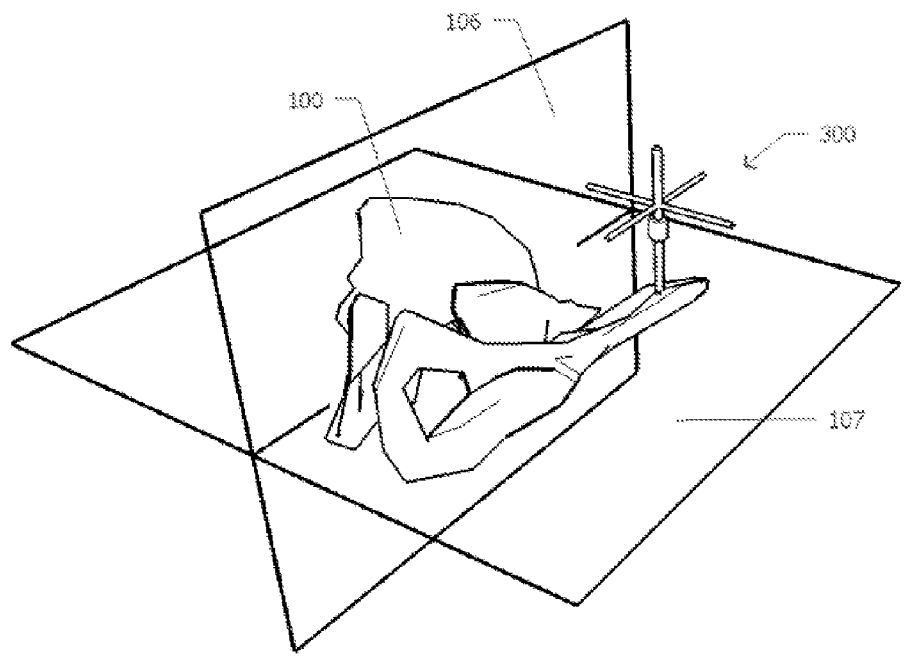
FIG. 6 shows a human pelvis and two anatomic planes, with a reference apparatus fixed to the pelvis, wherein the indicator is parallel to the shown anatomic planes.

FIG. 6 shows a pelvis 100 and two anatomic planes 106, 107. To the left spina iliaca anterior superior 101 a reference apparatus 300 is fixed by insertion therein (cf. description with respect to FIG. 5). In the reference apparatus 300 the indicator 302 has a predetermined orientation with respect to the anchor 301 due to their connection system. Due to this, the anchor 301 and the indicator 302 have a predetermined position and relationship (parallel and/or perpendicular—governed by the predetermined direction imposed by the connection to the orientation apparatus) to the anatomic planes 106, 107, an therewith to all not shown anatomic planes and/or axes (105, 109, 110, 108) of the subjects body portion to be mapped (here the pelvis). Since and as long as the pelvis 100 and the reference apparatus 300 are fixed to each other the anatomic planes and axes of the pelvis are clarified and made visible, in particular to the orthopaedic surgeon, possibly during the entire surgical procedure. Due to the fixation, the clarification and indication also validly applies when the pelvis is moved during surgery; the indication is substantially independent of positional or posture changes of the patient (for the desired surgical procedure) or other possible movements of the pelvis. The reference apparatus 300 thus provides an important contribution to the possibilities of accurate alignment and/or placement of an implant, in particular an acetabular cup.

In the above description a number of preferred embodiments are described. The disclosure is however not limited to these embodiments and any embodiment within the scope of the appended claims is considered to fall into the spirit and breadth of this disclosure.

For instance, an orientation apparatus having a general T-shape instead of the above-described triangular shape may be envisioned. Another example is a reference apparatus of which the indicator is arranged for indicating only a single axis (cf. FIG. 8), possibly comprising a laser or onto which a laser is connectable (e.g. having mated connectors), for determination of a direction over relatively long distances (longer than the mechanical size of the indicator), which may further increase accuracy of the determination.

Small contact surfaces, e.g. rounded or pointed tips are preferred for contact surfaces of the probes. In case the probes have relatively wide contact surfaces, e.g. flat or disc-like contact surfaces, two probes may suffice for defining a plane sufficiently reliably.

Elements and aspects discussed for or in relation with a particular embodiment may be suitably combined with elements and aspects of other embodiments, unless explicitly stated otherwise.

The invention claimed is:

1. A navigation system for accurate placing of an implant during surgery,
comprising an orientation apparatus and a reference apparatus,
wherein the reference apparatus comprises an anchor for fixing the reference apparatus to a predetermined feature of the subjects body, and at least one indicator for indicating at least one reference plane or axis,
wherein the orientation apparatus comprises a number of probes for contacting a number of predetermined features of a subjects body and defining a plane,
wherein at least one of the orientation apparatus and the reference apparatus comprises at least one connector for connecting the orientation apparatus and the anchor such that, when connected, relative translation of the connector and the anchor along a predetermined direction with respect to the plane defined by the probes is allowed and relative rotation of the connector and the anchor about that predetermined direction is prevented.

2. The navigation system of claim 1, wherein the at least one connector comprises a through hole defining the predetermined direction and wherein the anchor comprises at least a connection portion mated to the through hole.

3. The navigation system of claim 2, wherein the through hole has a non-circular cross-sectional shape and the connection portion of the anchor has a mated non-circular cross-sectional shape.

4. The navigation system of claim 1, wherein a probe comprises the at least one connector.

5. The navigation system of claim 1, wherein the predetermined direction is substantially normal to the plane.

6. The navigation system of claim 1, wherein the orientation apparatus comprises a first, second and third probe connected to each other with at least two connecting members, wherein the connecting members are adjustable such that the first probe may contact a first predetermined feature of the subjects body, e.g. the os pubis, the second probe may contact a second predetermined feature of the subjects body, e.g. the left spina iliaca anterior superior and the third probe may contact a third predetermined feature of the subjects body, e.g. the right spina iliaca anterior superior, concurrently.

7. The navigation system of claim 6, wherein at least one connecting member is length-adjustable.

8. The navigation system of claim 6, wherein at least two connecting members are arranged at an angle to each other and wherein the angle is adjustable.

9. The navigation system of claim 7, wherein at least two connecting members are arranged at an angle to each other and wherein the angle is adjustable.

10. The navigation system of claim 6, wherein at least a portion of at least one of the connecting members extends offset from the plane.

11. The navigation system of claim 7, wherein at least a portion of at least one of the connecting members extends offset from the plane.

12. The navigation system of claim 1, wherein at least one probe of the orientation apparatus is height-adjustable with respect to a least one other probe and/or at least one connecting member.

13. The navigation system of a claim 1, wherein the reference apparatus comprises plural anchoring portions for fixing the reference apparatus to the subjects body.

14. The navigation system of claim 1, wherein the anchor and the indicator of the reference apparatus are irrotationally coupled together.

15. The navigation system of claim 1, wherein the anchor and the indicator of the reference apparatus are releasably coupled together.

16. The navigation system of claim 1, wherein the indicator of the reference apparatus is arranged for indicating at least one of at least one plane and at least one axis.

17. An orientation apparatus for use in the navigation system of claim 1,
wherein the orientation apparatus comprises a number of probes and at least one connector,
the probes being configured for contacting a number of predetermined features of a subjects body and defining a plane,
the at least one connector being configured for connecting the orientation apparatus and a reference apparatus comprising an anchor for fixing the reference apparatus to a predetermined feature of the subjects body, such that, when connected, relative translation of the connector and the anchor along a predetermined direction with respect to the plane defined by the probes is allowed and relative rotation of the connector and the anchor about that predetermined direction is prevented.

18. A reference apparatus, for use in the navigation system of claim 1,
wherein the reference apparatus comprises at least one connector, an anchor for fixing the reference apparatus to a predetermined feature of the subjects body, and at least one indicator for indicating at least one reference plane or axis,
wherein the at least one connector is configured for connecting the anchor and an orientation apparatus having a number of probes such that, when connected, relative translation of the orientation apparatus and the anchor along a predetermined direction with respect to the plane defined by the probes is allowed and relative rotation of the connector and the anchor about that predetermined direction is prevented.

* * * * *